(12) United States Patent
Lee et al.

(10) Patent No.: US 9,295,452 B2
(45) Date of Patent: Mar. 29, 2016

(54) METHOD AND APPARATUS FOR CORRECTING ULTRASOUND IMAGES BY USING INTEREST INDEX MAP

(75) Inventors: Yoon-chang Lee, Gangwon-do (KR); Kurt Sandstrom, Gangwon-do (KR)

(73) Assignee: Samsung Medison Co., Ltd., Gangwon-do (KR)

( * ) Notice: Subject to any disclaimer, the term of this patent is extended or adjusted under 35 U.S.C. 154(b) by 789 days.

(21) Appl. No.: 13/482,520

(22) Filed: May 29, 2012

(65) Prior Publication Data

US 2013/0137982 A1    May 30, 2013

(30) Foreign Application Priority Data

Nov. 30, 2011    (KR) .................. 10-2011-0127229

(51) Int. Cl.
- A61B 8/00    (2006.01)
- A61B 8/08    (2006.01)
- G01S 7/52    (2006.01)

(52) U.S. Cl.
CPC ................. *A61B 8/54* (2013.01); *A61B 8/5207* (2013.01); *A61B 8/5246* (2013.01); *G01S 7/52033* (2013.01); *A61B 8/463* (2013.01)

(58) Field of Classification Search
USPC .................................. 600/407, 437, 443–447
See application file for complete search history.

(56) References Cited

U.S. PATENT DOCUMENTS

| | | | |
|---|---|---|---|
| 5,482,046 A | 1/1996 | Deitrich | |
| 6,413,218 B1 * | 7/2002 | Allison et al. | 600/443 |
| 2001/0025143 A1 | 9/2001 | Suzuki | |
| 2002/0022780 A1 * | 2/2002 | Kawagishi et al. | 600/443 |
| 2005/0055178 A1 * | 3/2005 | Phillips et al. | 702/189 |
| 2005/0187476 A1 | 8/2005 | Chomas et al. | |
| 2006/0030779 A1 | 2/2006 | Chomas et al. | |
| 2007/0196282 A1 | 8/2007 | Oliver | |
| 2010/0016719 A1 | 1/2010 | Freiburger et al. | |

FOREIGN PATENT DOCUMENTS

| | | |
|---|---|---|
| JP | 5-29508 U | 4/1993 |
| JP | 10-080424 A | 3/1998 |
| JP | 3378308 B2 | 2/2003 |
| JP | 2009-142474 A | 7/2009 |

OTHER PUBLICATIONS

European Office Action issued in European Application No. 12 161 586.8 issued Feb. 13, 2014.
Korean Notice of Allowance, w/ English translation thereof, issued in Korean Patent Application No. KR 10-2011-0127229 dated Dec. 20, 2012.
Extended European Search Report issued in European Application No. 12161586.8 dated Apr. 3, 2013.

* cited by examiner

*Primary Examiner* — Joel F Brutus
(74) *Attorney, Agent, or Firm* — McDermott Will & Emery LLP (57) ABSTRACT

A method of correcting ultrasound images, the method including the operations of, by an ultrasound output unit, outputting an ultrasound signal to a target object; obtaining an mechanical index (MI) map indicating a correlation between depth values according to a travel direction of the ultrasound signal, and MI values by the ultrasound signal; and adjusting a gain value of an ultrasound echo signal corresponding to the ultrasound signal by using a reverse MI map that is obtained by reversing the MI map, so as to allow the MI values, which are displayed on the MI map, to be a virtually constant MI value with respect to the depth values.

19 Claims, 5 Drawing Sheets

METHOD AND APPARATUS FOR CORRECTING ULTRASOUND IMAGES BY USING INTEREST INDEX MAP

CROSS-REFERENCE TO RELATED PATENT APPLICATION

This application claims the benefit of Korean Patent Application No. 10-2011-0127229, filed on Nov. 30, 2011, in the Korean Intellectual Property Office, the disclosure of which is incorporated herein in its entirety by reference.

BACKGROUND OF THE INVENTION

1. Field of the Invention

The present invention relates to a method and apparatus for correcting ultrasound images by using an interest index map.

2. Description of the Related Art

An ultrasound diagnosis apparatus delivers an ultrasound signal from a body surface of a target object to a predetermined part in the body, and then obtains an image of tomography or hematocele of a soft tissue by using information of the ultrasound signal reflected from a tissue in the body.

The ultrasound diagnosis apparatus is advantageous in that it is small, is inexpensive, and displays in real-time. Also, the ultrasound diagnosis apparatus is not harmful such as radio-activity and thus is safe, so that it is widely used together with an X-ray diagnosis apparatus, a computerized tomography (CT) scanner, a magnetic resonance image (MRI) apparatus, a nuclear medicine diagnosis apparatus, and the like.

In general, an output (a transmission voltage, a pressure, and energy) of the ultrasound diagnosis apparatus is limited by and is decided according to an international reference (e.g., a mechanical index (MI)). Here, the MI is an index of quantification of mechanical affects by ultrasound with respect to a human body.

Another example of the quantification of mechanical affects by ultrasound with respect to a human body is a thermal index (TI). According to a common level, international permission levels of the MI and the TI are less than 1.9 and 6.0, respectively.

The ultrasound diagnosis apparatus further precisely diagnoses a target object by increasing a transmission voltage of an ultrasound signal which is output from a pulser. In this regard, as the transmission voltage is increased, a sensitivity of an image is improved but the MI or an acoustic pressure (a pressure generated by ultrasound that passes through a medium) is increased.

Also, when an ultrasound signal output from the ultrasound diagnosis apparatus passes through a medium such as a human body, interest indexes such as the MI, the acoustic pressure, the TI, and the like may not have regular dispersion in one frame, according to a focus forming method or an interest depth of an ultrasound beam.

That is, ultrasound images based on a received ultrasound echo signal do not have a uniform brightness or quality of some of the ultrasound images may deteriorate.

SUMMARY OF THE INVENTION

The present invention provides a method of correcting ultrasound images by using an interest index map, and more particularly, to a method and apparatus for correcting ultrasound images by using one of a mechanical index (MI) map, an acoustic pressure map, and a thermal index (TI) map.

According to an aspect of the present invention, there is provided a method of correcting ultrasound images, the method including operations of, by an ultrasound output unit, outputting an ultrasound signal to a target object; obtaining a MI map indicating a correlation between depth values according to a travel direction of the ultrasound signal, and MI values by the ultrasound signal; and adjusting a gain value of an ultrasound echo signal corresponding to the ultrasound signal by using a reverse MI map that is obtained by reversing the MI map, so as to allow the MI values, which are displayed on the MI map, to be a virtually constant MI value with respect to the depth values.

The method may further include operations of generating ultrasound image of the target object based on the ultrasound echo signal having the adjusted gain value; and displaying the ultrasound image.

The method may include operations of obtaining an acoustic pressure map indicating a correlation between depth values according to a travel direction of the ultrasound signal, and acoustic pressure values by the ultrasound signal; and adjusting a gain value of an ultrasound echo signal corresponding to the ultrasound signal by using a reverse acoustic pressure map that is obtained by reversing the acoustic pressure map.

The method may include operations of obtaining a TI map indicating a correlation between depth values according to a travel direction of the ultrasound signal, and TI values by the ultrasound signal; and adjusting a gain value of an ultrasound echo signal corresponding to the ultrasound signal by using a reverse TI map that is obtained by reversing the TI map.

The method may include operations of, by the ultrasound output unit, outputting ultrasound signals having a first focus and a second focus; obtaining a first MI map and a second MI map that correspond to the first focus and the second focus, respectively; adjusting a gain value of an ultrasound echo signal corresponding to the first focus by using a first reverse MI map that is obtained by reversing the first MI map, so as to allow the MI values, which are displayed on the first MI map, to be a virtual first MI value with respect to the depth values; and adjusting a gain value of an ultrasound echo signal corresponding to the second focus by using a second reverse MI map that is obtained by reversing the second MI map, so as to allow the MI values, which are displayed on the second MI map, to be a virtual second MI value with respect to the depth values.

The virtual first MI value may be decided based on a maximum MI value of the first MI map, and the virtual second MI value may be decided based on a maximum MI value of the second MI map.

The method may further include operations of determining whether the virtual first MI value and the virtual second MI value are equal to each other; and, if not equal, re-adjusting the adjusted gain value of the ultrasound echo signal corresponding to the first focus or the adjusted gain value of the ultrasound echo signal corresponding to the second focus, so as to allow the virtual first MI value and the virtual second MI value to be equal to each other.

The method may include operations of generating the ultrasound image of the target object by blending the ultrasound echo signal having the adjusted gain value corresponding to the first focus with the ultrasound echo signal having the adjusted gain value corresponding to the second focus; and displaying the ultrasound image.

The method may further include operations of adjusting a first ultrasound transmission voltage corresponding to the first focus or a second ultrasound transmission voltage corresponding to the second focus, so as to allow a first maximum MI corresponding to the first focus and a second maximum MI corresponding to the second focus to be equal to each other.

According to another aspect of the present invention, there is provided an ultrasound images correcting apparatus including an ultrasound output unit for outputting an ultrasound signal to a target object; a map obtaining unit for obtaining a MI map indicating a correlation between depth values according to a travel direction of the ultrasound signal, and MI values by the ultrasound signal; and a control unit for adjusting a gain value of an ultrasound echo signal corresponding to the ultrasound signal by using a reverse MI map that is obtained by reversing the MI map, so as to allow the MI values, which are displayed on the MI map, to be a virtually constant MI value with respect to the depth values.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Terms or words used in the following description should not be construed as being limited to common or general meanings but should be construed as fully satisfying the concept of the invention. In the following description, the applicant arbitrarily selects some terms or words, and in those cases, the detailed meaning are provided here.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

In the following description, "user" may indicate a medical expert including a doctor, a nurse, a clinical pathologist, a medical image expert, or the like but is not limited thereto.

In the following description, "interest index" may include a mechanical index (MI), a thermal index (TI), or an acoustic pressure.

Hereinafter, the present invention will be described in detail by explaining exemplary embodiments of the invention with reference to the attached drawings. In the following description, functions or constructions that are not related to the present invention are omitted, and like reference numerals in the drawings denote like elements.

Expressions such as "at least one of," when preceding a list of elements, modify the entire list of elements and do not modify the individual elements of the list.

Figure 1:
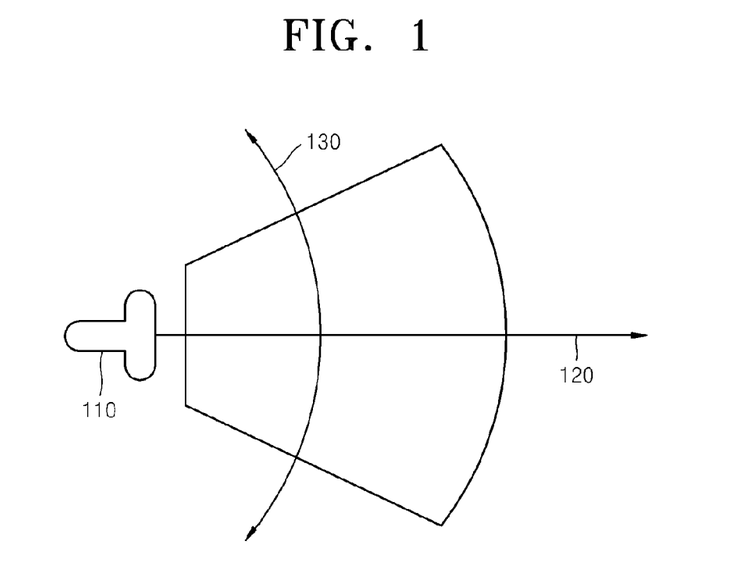
FIG. 1 is a conceptual drawing describing a reference axis with respect to obtaining or displaying an interest index map according to an embodiment of the present invention.

FIG. 1 is a conceptual drawing describing a reference axis with respect to obtaining or displaying an interest index map according to an embodiment of the present invention.

A direction in which ultrasound that is output from an ultrasound output unit 110 of an ultrasound images correcting apparatus travels may be an axis of depth values 120 according to the present embodiment. The ultrasound output unit 110 may be included in a probe.

The axis of the depth values 120 may correspond to a direction in which the depth values 120 that start in an interface of a target object to be diagnosed by using the ultrasound images correcting apparatus increase toward the inside of a soft tissue.

The probe may transmit an ultrasound beam to the target object along scan lines 130, wherein the ultrasound beam is generated in a manner that transmission pulse signals are input after an appropriate delay. In this case, the ultrasound images correcting apparatus may generate a two-dimensional (2D) map or a three-dimensional (3D) map based on interest index values corresponding to the depth values 120 and the scan lines 130.

According to the present embodiment, the probe may be at least one of a 1-dimensional (1D) probe, a 1.5D probe, and a 2D (matrix) probe.

Figure 2:
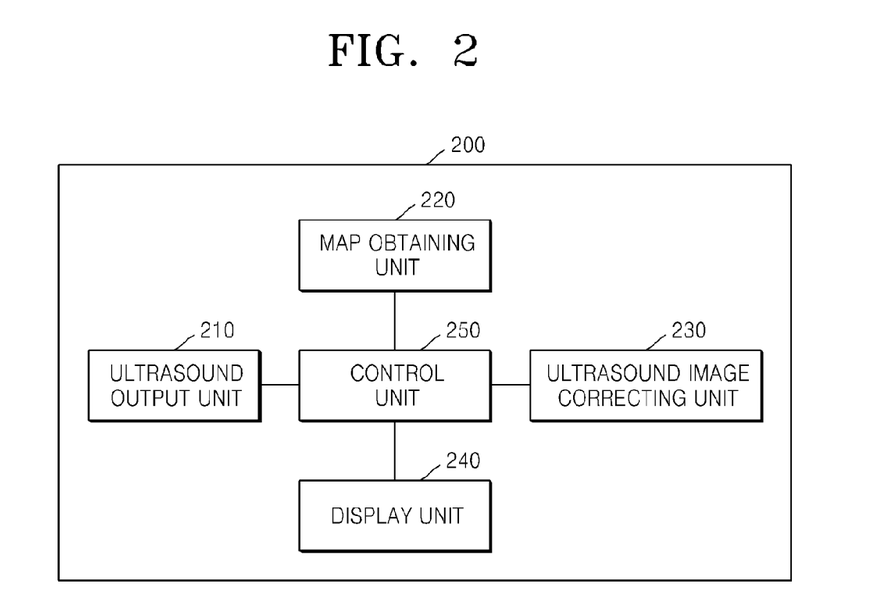
FIG. 2 is a block diagram illustrating a structure of an ultrasound images correcting apparatus according to an embodiment of the present invention.

FIG. 2 is a block diagram illustrating a structure of an ultrasound images correcting apparatus 200 according to an embodiment of the present invention.

As illustrated in FIG. 2, the ultrasound images correcting apparatus 200 may include an ultrasound output unit 210, a map obtaining unit 220, an ultrasound image correcting unit 230, a display unit 240, and a control unit 250. However, not every element of the ultrasound images correcting apparatus 200 is necessary. More elements or less elements than the aforementioned elements may embody the ultrasound images correcting apparatus 200.

The ultrasound output unit 210 may output an ultrasound signal to a target object. The ultrasound output unit 210 may output the ultrasound signal having multiplex focuses. Also, the ultrasound output unit 210 may output the ultrasound signal by using pulses having various wavelengths, or may output the ultrasound signal based on a transmission voltage having various levels.

In a case of the multiplex focuses, the ultrasound output unit 210 may adjust a voltage of a transmission ultrasound signal so as to allow maximum MIs at the multiplex focuses to be same. That is, in order to maintain the same MIs or acoustic pressures, the voltage of the transmission ultrasound signal may vary according to positions of the multiplex focuses.

The map obtaining unit 220 may obtain an interest index map. The interest index map according to the present embodiment may include an MI map, a TI map, and an acoustic pressure map. The MI map is visual data indicating a correlation between the depth values 120 and an MI according to a travel direction of an ultrasound signal output from the ultrasound output unit 210. The acoustic pressure map is visual data indicating a correlation between the depth values 120 and an acoustic pressure according to the travel direction of the ultrasound signal output from the ultrasound output unit 210.

The map obtaining unit 220 may calculate an interest index according to the ultrasound signal output from the ultrasound output unit 210, and may generate the interest index map by using the calculated interest index.

For example, the map obtaining unit 220 may calculate at least one of an MI, a TI, and an acoustic pressure with respect to depth values of an axial direction in which ultrasound is transmitted. In this case, the map obtaining unit 220 may continuously calculate the interest index for all depth values, or may select some of depth values, may calculate the interest index for only the selected depth values, and may interpolate the rest of the interest indexes, which are not calculated, by using the calculated interest index.

In another embodiment, the map obtaining unit 220 may receive an interest index map from an external source.

The TI may include a TI-soft tissue (TIs), Ti-bone (TIb), and TI-cranial bone (TIc). Thus, according to the present embodiment, the map obtaining unit 220 may obtain each of a TIs map, a TIb map, and a TIc map, or may only obtain one of the TIs map, the TIb map, and the TIc map according to a user's selection.

Also, the map obtaining unit 220 may extract a representative TI from among the TIs, the TIb, and the TIc, and may obtain a representative TI map with respect to the extracted representative TI. In the present embodiment, the map obtaining unit 220 may extract a greatest value from among the TIs, the TIb, and the TIc, as the representative TI.

The interest index map may include a 2D map or a 3D map with respect to each of the MI map, the acoustic pressure map, and the TI map.

In a case where ultrasound signals having multiplex focuses are output, the map obtaining unit 220 may obtain a plurality of interest index maps corresponding to the multiplex focuses, respectively.

For example, in a case where the ultrasound output unit 210 outputs ultrasound signals having a first focus and a second focus with respect to one scan line, the map obtaining unit 220 may obtain a first interest index map and a second interest index map that correspond to the first focus and the second focus, respectively.

The ultrasound image correcting unit 230 may generate an ultrasound image with respect to the target object by using, an ultrasound echo signal of which a gain value is adjusted. The ultrasound images correcting apparatus 200 adjusts the gain value of the ultrasound echo signal so as to allow an interest index, which is displayed on an interest index map, to be a virtually constant value with respect to all depth values. Thus, by using the ultrasound echo signal of which a gain value is adjusted, it is possible to obtain uniform ultrasound images with respect to depth values or scan lines.

That is, according to the present embodiment, the adjustment of the gain value of the ultrasound echo signal may create the same effect as a case in which a power of the ultrasound signal that is output from the ultrasound output unit 210 is regularly adjusted with respect to the depth values or the scan lines.

In a case where multiplex focuses are used, the ultrasound image correcting unit 230 blends ultrasound echo signals that have adjusted gain values and that correspond to the multiplex focuses, respectively, so that the ultrasound image correcting unit 230 may correct ultrasound image with respect to a target object.

For example, the ultrasound image correcting unit 230 may correct the ultrasound image with respect to the target object by blending an ultrasound echo signal of which a gain value corresponding to a first focus is adjusted with an ultrasound echo signal of which a gain value corresponding to a second focus is adjusted.

That is, according to the present embodiment, in a case where the multiplex focuses are used, the ultrasound image correcting unit 230 does not simply perform zone-blending on the ultrasound echo signals corresponding to the multiplex focuses, respectively, but adjusts a gain value of each of the ultrasound echo signals and then performs weighted zone-blending. By doing so, the ultrasound image correcting unit 230 may correct the ultrasound image with respect to the target object.

The display unit 240 may display the ultrasound image with respect to the target object. According to the present embodiment, the display unit 240 may display the ultrasound images that have been corrected by adjusting the gain value of the ultrasound echo signal.

Also, the display unit 240 may display the interest index map. Here, the display unit 240 may selectively display at least one from among the interest index map including the MI map, the TI map, and the acoustic pressure map or may display all of the three interest index maps.

The display unit 240 may be implemented by a monitor of a general ultrasound diagnosis apparatus or, if required, the display unit 240 may be implemented by a user interface.

In the present embodiment, if a display mode indicates a single mode, the display unit 240 may display the ultrasound images together with the interest index (i.e., the MI, the acoustic pressure, and the TI) on a specific region. In another embodiment, if a display mode indicates a dual mode, the ultrasound images and the interest index may be separately displayed on different screens.

Also, the display unit 240 may provide a magnified image of a specific part of the ultrasound images or a specific part of the interest index.

According to the present embodiment, the display unit 240 may selectively display at least one of the TIs map and the TIb map, and the TIc map. Also, the display unit 240 may selectively display the TI map and the thermal dose map.

The display unit 240 may display at least one of a 1D map, a 2D map, and a 3D map with respect to each of the MI, the acoustic pressure, and the TI, or may display at least one of a contour line map, a gray map, a mesh map, and a color map.

The control unit 250 may adjust the gain value of the ultrasound echo signal corresponding to the output ultrasound signal. According to the present embodiment, the control unit 250 may adjust the gain value of the ultrasound echo signal according to the depth values 120 or the scan lines 130 so as to obtain the ultrasound images that are uniform.

For example, in order to allow the interest index, which is displayed on the interest index map, to be a virtually constant interest index value with respect to all depth values, the control unit 250 may adjust the gain value of the ultrasound echo signal corresponding to the output ultrasound signal by using a reverse interest index map that is obtained by reversing the interest index map. That is, the control unit 250 may adjust the gain value of the ultrasound echo signal by using at least one of a reverse MI map, a reverse TI map, and a reverse acoustic pressure map.

According to the present embodiment, a virtual interest index value with respect to the ultrasound echo signal having the adjusted gain value may be constant. This is because a case in which sensitivity of the ultrasound images becomes uniform by adjusting the gain value by using software may achieve a similar effect to a case in which power level of transmission signals are equally adjusted by using hardware.

The virtual interest index value according to the present embodiment does not mean an actual interest index value by the output ultrasound signal. In a case where the ultrasound images are corrected to have the uniform sensitivity, the virtual interest index value corresponds to a virtual transmission voltage that is required to obtain the corrected ultrasound images.

For example, in a case where the ultrasound images are uniformly corrected by adjusting the gain value of the ultrasound echo signal, a transmission voltage of 140 Vpp is required for all depth values or all scan lines so as to obtain the same sensitivity as the corrected ultrasound images, and if an MI value corresponding to 140 Vpp is 1.4, a virtual MI may be 1.4.

That is, in a case where MIs shown in the MI are different, e.g., 1.2, 1.3, 1.4, 1.3, and 1.2 according to the depth values, although the control unit 250 does not adjust the transmission voltage with respect to all depth values or all scan lines as 140 Vpp, the control unit 250 may obtain the uniform ultrasound images by adjusting the gain value of the ultrasound echo signal according to the depth values.

In the present embodiment, the virtual interest index value may be decided in consideration of a maximum interest index value displayed on the interest index map or an international permission reference for the interest index. That is, the virtual interest index value may be the maximum interest index value or a predetermined multiplied value of the maximum interest index value which does not exceed an international permission reference.

For example, when the maximum interest index value on the MI map is 1.2, the gain value of the ultrasound echo signal may be adjusted to allow the virtual interest index value with respect to all depth values to be 1.2 or 1.44 (=1.22×120%).

In a case where the multiplex focuses are used, the control unit 250 may adjust the gain values of the ultrasound echo signals that correspond to the multiplex focuses, respectively.

For example, it is assumed that the ultrasound output unit 210 outputs ultrasound signals having a first focus and a second focus. In this regard, in order to allow an interest index value, which is displayed on an interest index map corresponding to the first focus, to be a virtual first interest index value for all depth values, the control unit 250 may adjust a gain value of an ultrasound echo signal corresponding to the first focus by using a first reverse interest index map. Also, in order to allow an interest index value, which is displayed on an interest index map corresponding to the second focus, to be a virtual second interest index value for all depth values, the control unit 250 may adjust a gain value of an ultrasound echo signal corresponding to the second focus by using a second reverse interest index map.

In this case, the control unit 250 may determine whether the virtual first interest index value corresponding to the first focus is the same as the virtual second interest index value corresponding to the second focus.

According to the present embodiment, the virtual first interest index value and the virtual second interest index value may be equal or different. In a case where they are different from each other, although the ultrasound echo signal having the adjusted gain value corresponding to the first focus is blended with the ultrasound echo signal having the adjusted gain value corresponding to the second focus, sensitivity of corrected ultrasound images may not be uniform.

Thus, in order to allow the virtual first interest index value and the virtual second interest index value to be equal to each other, the control unit 250 may re-adjust the gain value of the ultrasound echo signal corresponding to the first focus or the second focus.

Also, in order to allow a first maximum interest index value corresponding to the first focus and a second maximum interest index value corresponding to the second focus to be equal to each other, the control unit 250 may adjust a first ultrasound transmission voltage corresponding to the first focus or a second ultrasound transmission voltage corresponding to the second focus.

That is, the control unit 250 adjusts an ultrasound transmission voltage at each focus, thereby actually changing the MI, the acoustic pressure, and the TI. In this case, since a virtual first MI value and a virtual second MI value that are decided based on a maximum MI may be the same, the control unit 250 may not re-adjust the gain value of the ultrasound echo signal corresponding to the first focus or the second focus.

Figure 3:
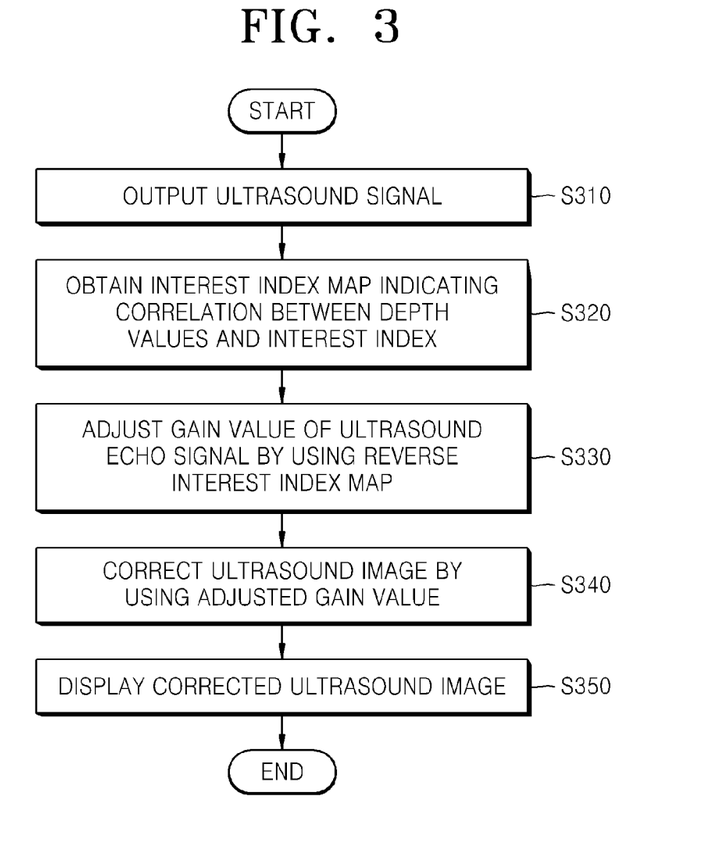
FIG. 3 is a flowchart describing a method of correcting ultrasound images, according to an embodiment of the present invention.

FIG. 3 is a flowchart describing a method of correcting ultrasound images, according to an embodiment of the present invention.

Referring to FIG. 3, the method includes operations that are chronologically performed in the ultrasound images correcting apparatus 200 of FIG. 2. Thus, although some features are omitted in the description below, if the features are described above with reference to the ultrasound images correcting apparatus 200 of FIG. 2, the features are also applied to the method of FIG. 3.

As illustrated in FIG. 3, according to the present embodiment, the ultrasound images correcting apparatus 200 may output an ultrasound signal from the ultrasound output unit 210 to a target object (operation S310).

Here, the ultrasound images correcting apparatus 200 may obtain an interest index map indicating a correlation between depth values according to a travel direction of the output ultrasound signal, and an interest index by the output ultrasound signal (operation S320). The interest index map may include an MI map, a TI map, and an acoustic pressure map.

Figure 4:
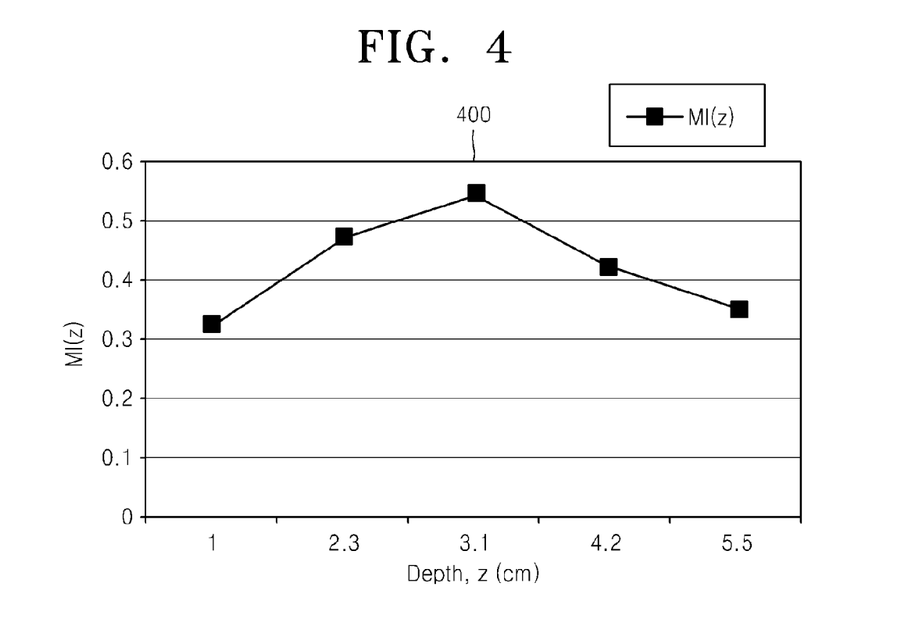
FIG. 4 is a diagram illustrating a displayed mechanical index (MI) map, according to an embodiment of the present invention.

The interest index displayed on the interest index map may vary according to the depth values. For example, as illustrated in FIG. 4, an MI may vary according to the depth values.

The ultrasound images correcting apparatus 200 uses a focus beam, and thus, the MI at the depth value corresponding to a focus may be a maximum value. The acoustic pressure map may have a similar graph as that of the MI map in FIG. 4. Also, in a case of the TI map, a graph of the TI map may be similar to that of the MI map or the acoustic pressure map, however, a TI may be greater at a depth value that is lower than the depth value corresponding to the focus.

The ultrasound images correcting apparatus 200 may generate the interest index map as a 1D map, a 2D map, or a 3D map. For example, in a case where the ultrasound images correcting apparatus 200 uses a 1D probe, the ultrasound images correcting apparatus 200 may calculate interest indexes corresponding to the depth values 120 and the scan lines 130 and then may generate a 2D map. In this case, the ultrasound images correcting apparatus 200 may generate a 3D map by stereographically expressing the interest indexes corresponding to the depth values 120 and the scan lines 130 in the form of a net. In another embodiment, the ultrasound images correcting apparatus 200 may express the interest indexes as an interest index map that is not fixed but varies according to time (frame) while ultrasound scanning is performed. That is, the ultrasound images correcting apparatus 200 may calculate interest indexes according to the depth values 120, the scan lines 130, and time, and then may generate a 3D map.

In a case where the ultrasound images correcting apparatus 200 uses a 1.5D probe or a 2D (matrix) probe, the ultrasound images correcting apparatus 200 may express interest indexes with respect to an axial direction (depth values), a lateral direction (scan line values), and an elevation direction, as the 3D map.

The ultrasound images correcting apparatus 200 may express the interest index map as one of various types including a contour line map, a gray map, a mesh map, and a color map.

Referring back to FIG. 3, in order to allow an interest index value, which is displayed on the interest index map, to be a virtually constant interest index value with respect to all depth values, the ultrasound images correcting apparatus 200 may adjust a gain value of an ultrasound echo signal by using a reverse interest index map (operation S330).

Figure 5:
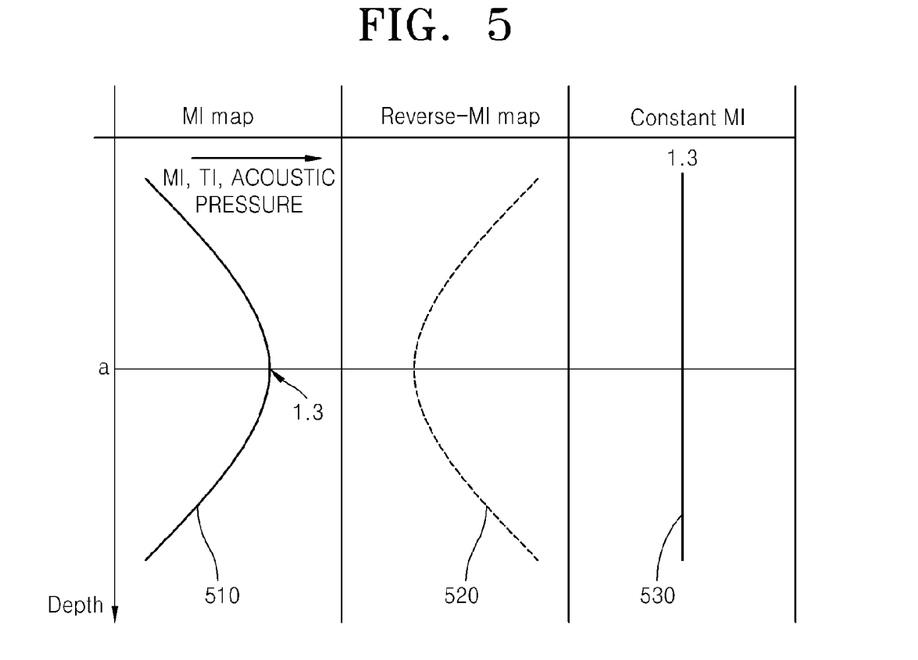
FIG. 5 is a diagram illustrating a reverse interest index map, according to an embodiment of the present invention.

For example, as illustrated in FIG. 5, the ultrasound images correcting apparatus 200 may obtain an MI map 510 having a maximum MI value of 1.3 at a depth value a. In this case, the ultrasound images correcting apparatus 200 may adjust the gain value of the ultrasound echo signal by using a reverse MI map 520, so as to allow MIs, which correspond to all depth values, to be a constant value (e.g., a maximum MI value). Referring to FIG. 5, virtual MIs 530 with respect to all depth values become 1.3, which is the maximum MI value of the MI map 510.

Referring back to FIG. 3, the ultrasound images correcting apparatus 200 may correct ultrasound image of the target object by using the adjusted gain value (operation S340). That is, the ultrasound images correcting apparatus 200 corrects the ultrasound image by re-generating the ultrasound image of the target object by using the ultrasound echo signal having the adjusted gain value.

According to the present embodiment, the ultrasound images correcting apparatus 200 may display the corrected ultrasound images (operation S350). That is, the ultrasound images correcting apparatus 200 may display the ultrasound images that are re-generated by adjusting the gain value of the ultrasound echo signal.

Figure 6:
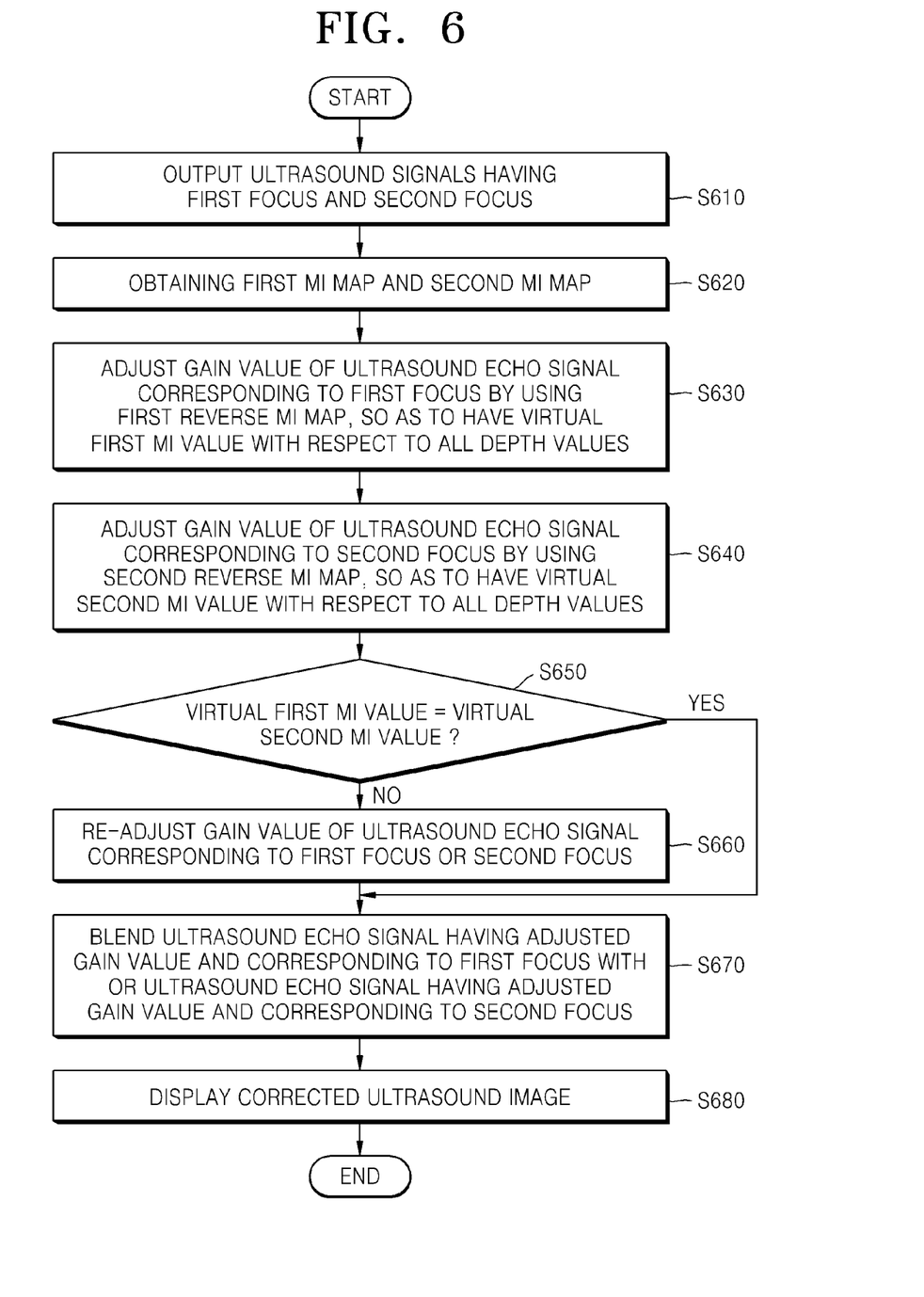
FIG. 6 is a flowchart describing a method of correcting ultrasound images having multiplex focuses, according to another embodiment of the present invention.

FIG. 6 is a flowchart describing a method of correcting ultrasound images having multiplex focuses, according to another embodiment of the present invention.

Referring to FIG. 6, the method includes operations that are chronologically performed in the ultrasound images correcting apparatus 200 of FIG. 2. Thus, although some features are omitted in the description below, if the features are described above with reference to the ultrasound images correcting apparatus 200 of FIG. 2, the features are also applied to the method of FIG. 6.

As illustrated in FIG. 6, according to the present embodiment, the ultrasound images correcting apparatus 200 may output ultrasound signals having a first focus and a second focus from the ultrasound output unit 210 (operation S610).

In this case, the ultrasound images correcting apparatus 200 may obtain a first interest index map and a second interest index map that correspond to the first focus and the second focus, respectively (operation S620). The first interest index map and the second interest index map may include at least one of an MI map, a TI map, and an acoustic pressure map. Hereinafter, an MI is described as an example of an interest index.

According to the present embodiment, the ultrasound images correcting apparatus 200 may adjust a gain value of an ultrasound echo signal corresponding to the first focus by using a first reverse MI map, so as to allow MI values, which are displayed on a first MI map, to be a virtual first MI value with respect to all depth values (operation S630).

Also, the ultrasound images correcting apparatus 200 may adjust the gain value of the ultrasound echo signal corresponding to the second focus by using a second reverse MI map, so as to allow MI values, which are displayed on a second MI map, to be a virtual second MI value with respect to all depth values (operation S640).

Here, the virtual first MI value may be decided based on a maximum MI value of the first MI map, and the virtual second MI value may be decided based on a maximum MI value of the second MI map.

According to the present embodiment, the ultrasound images correcting apparatus 200 may determine whether the virtual first MI value and the virtual second MI value are the same (operation S650).

If they are not the same, in order to allow the virtual first MI value and the virtual second MI value to be equal to each other, the ultrasound images correcting apparatus 200 re-adjusts the adjusted gain value of the ultrasound echo signal corresponding to the first focus or the adjusted gain value of the ultrasound echo signal corresponding to the second focus (operation S660).

Figure 7:
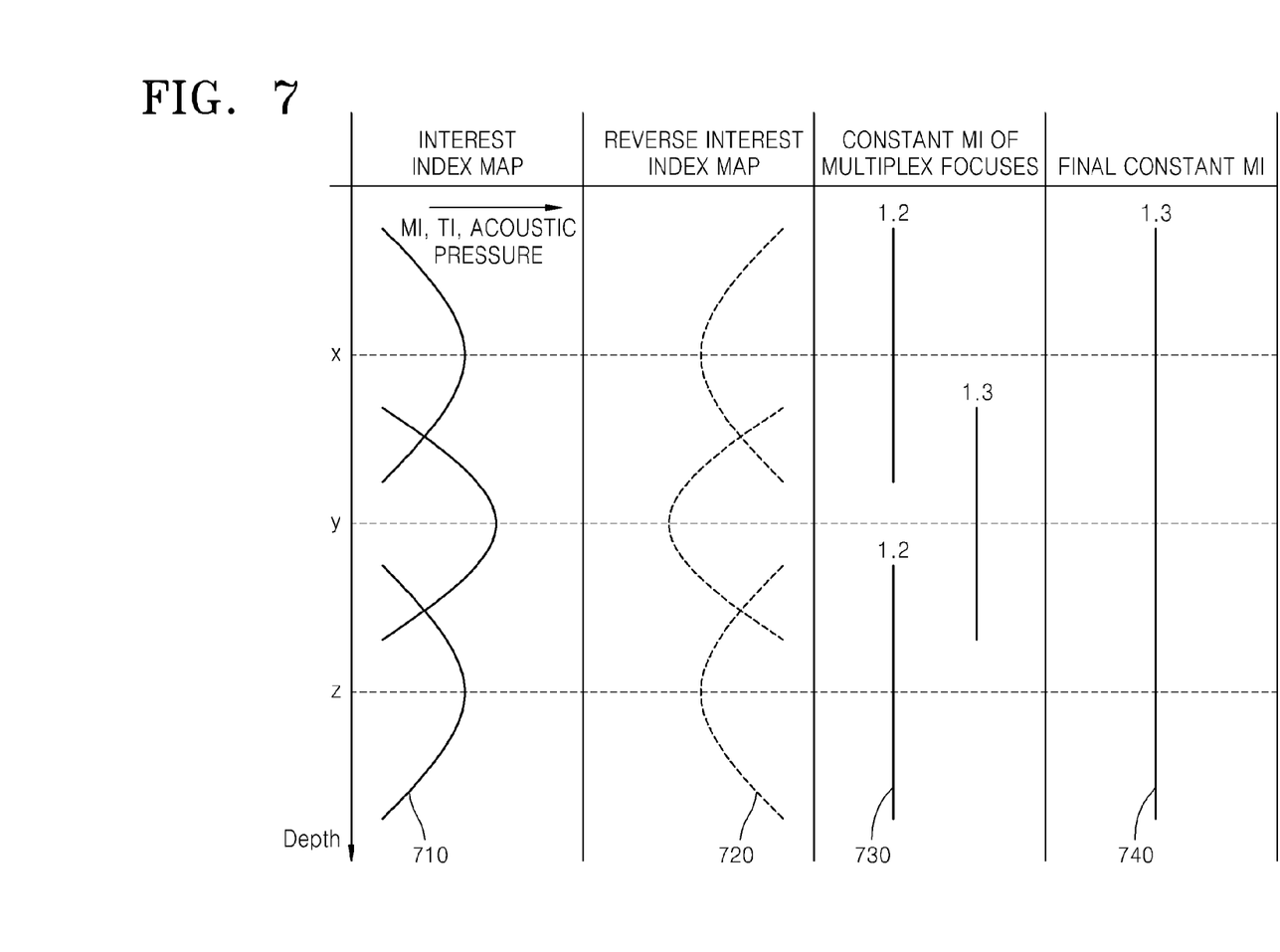
FIG. 7 is a diagram illustrating an interest index map and a reverse interest index map with respect to the multiplex focuses, according to an embodiment of the present invention.

For example, referring to FIG. 7, in a case where the ultrasound output unit 210 outputs ultrasound signals having an x-focus, a y-focus, and a z-focus, the ultrasound images correcting apparatus 200 may obtain MI maps 710 corresponding to the x-focus, the y-focus, and the z-focus, respectively.

In this case, the ultrasound images correcting apparatus 200 may adjust a gain value of an ultrasound echo signal corresponding to each focus by using reverse MI maps 720, so as to allow MIs, which correspond to all depth values, to be a constant value (e.g., a maximum MI).

In a case of the x-focus, in order to allow MIs at all depth values to be 1.2, which is a maximum MI value corresponding to the x-focus, the ultrasound images correcting apparatus 200 first adjusts a gain value of an ultrasound echo signal received at the x-focus.

In a case of the y-focus, in order to allow MIs at all depth values to be 1.3, which is a maximum MI value corresponding to the y-focus, the ultrasound images correcting apparatus 200 first adjusts a gain value of an ultrasound echo signal received at the y-focus.

In a case of the z-focus, in order to allow MIs at all depth values to be 1.2, which is a maximum MI value corresponding to the z-focus, the ultrasound images correcting apparatus 200 first adjusts a gain value of an ultrasound echo signal received at the z-focus.

After the first adjustment, a virtual MI corresponding to the x-focus becomes 1.2, a virtual MI corresponding to the y-focus becomes 1.3, and a virtual MI corresponding to the z-focus becomes 1.2.

Here, the virtual MIs that correspond to the x, y, and z focuses, respectively, have different values of 1.2 and 1.3 (refer to reference numeral 730 of FIG. 7). Thus, in order to allow all of the virtual MIs, which correspond to the x, y, and z focuses, to be 1.3, the ultrasound images correcting apparatus 200 secondly re-adjusts the ultrasound echo signal received at the x-focus and the ultrasound echo signal received at the z-focus.

The ultrasound images correcting apparatus 200 may adjust a first ultrasound transmission voltage corresponding to the first focus or a second ultrasound transmission voltage corresponding to the second focus, so as to allow a first maximum MI corresponding to the first focus and a second maximum MI corresponding to the second focus to be equal to each other.

For example, in a case where a maximum MI corresponding to the x-focus is 1.2, and a maximum MI corresponding to the y-focus is 1.3, the ultrasound images correcting apparatus 200 may increase the ultrasound transmission voltage corresponding to the x-focus so as to allow the maximum MI, which corresponds to the x-focus, to become 1.3 from 1.2.

In this case, the maximum MIs that correspond to the x, y, and z focuses, respectively, may be equalized by adjusting the ultrasound transmission voltages, so that the virtual MIs that correspond to the x, y, and z focuses, respectively, may be equalized. Thus, the ultrasound images correcting apparatus 200 may not re-adjust the gain value of the ultrasound echo signal.

Referring back to FIG. 6, the ultrasound images correcting apparatus 200 may re-generate the ultrasound image of the target object by blending the ultrasound echo signal having the adjusted gain value corresponding to the first focus with the ultrasound echo signal having the adjusted gain value corresponding to the second focus, and thus, may correct the ultrasound images (operation S670). In this case, the ultrasound images correcting apparatus 200 may display the corrected ultrasound images (operation S680).

Thus, according to the one or more embodiments of the present invention, it is possible to provide the uniform ultrasound images to the user by using the interest index map.

The invention can also be embodied as programmed commands to be executed in various computer means, and then can be recorded to a computer-readable recording medium. The computer-readable recording medium may include one or more of the programmed commands, data files, data structures, or the like. The programmed commands recorded to the computer-readable recording medium may be particularly designed or configured for the invention or may be well known to one of ordinary skill in the art. Examples of the computer-readable recording medium include magnetic media including hard disks, magnetic tapes, and floppy disks, optical media including CD-ROMs, and DVDs, magneto-optical media including floptical disks, and a hardware apparatus designed to store and execute the programmed commands in read-only memory (ROM), random-access memory (RAM), flash memories, and the like. Examples of the programmed commands include not only machine codes generated by a compiler but also include great codes to be executed in a computer by using an interpreter.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of correcting ultrasound images, the method comprising:
   outputting an ultrasound signal to a target object and receiving an ultrasound echo signal corresponding to the ultrasound signal;
   obtaining a mechanical index (MI) map indicating a correlation between depth values according to a travel direction of the ultrasound signal, and mechanical index (MI) values by the ultrasound signal;
   obtaining a reverse mechanical index (MI) map by reversing the mechanical index (MI) map; and
   adjusting a gain value of the ultrasound echo signal for each of the depth values by using the reverse mechanical index (MI) map.

2. The method of claim 1, further comprising:
   generating ultrasound image of the target object based on the ultrasound echo signal having the adjusted gain value; and
   displaying the ultrasound image.

3. The method of claim 1, wherein the method comprises:
   obtaining an acoustic pressure map indicating a correlation between depth values according to a travel direction of the ultrasound signal, and acoustic pressure values by the ultrasound signal; and
   adjusting a gain value of an ultrasound echo signal corresponding to the ultrasound signal by using a reverse acoustic pressure map that is obtained by reversing the acoustic pressure map.

4. The method of claim 1, wherein the method comprises:
   obtaining a thermal index (TI) map indicating a correlation between depth values according to a travel direction of the ultrasound signal, and thermal index (TI) values by the ultrasound signal; and
   adjusting a gain value of an ultrasound echo signal corresponding to the ultrasound signal by using a reverse thermal index (TI) map that is obtained by reversing the thermal index (TI) map.

5. The method of claim 1, wherein the method comprises:
   outputting ultrasound signals having a first focus and a second focus;
   obtaining a first mechanical index (MI) map and a second mechanical index (MI) map that correspond to the first focus and the second focus, respectively;
   adjusting a gain value of an ultrasound echo signal corresponding to the first focus by using a first reverse mechanical index (MI) map that is obtained by reversing the first mechanical index (MI) map, so as to allow the mechanical index (MI) values, which are displayed on the first mechanical index (MI) map, to be a virtual first mechanical index (MI) value with respect to the depth values; and
   adjusting a gain value of an ultrasound echo signal corresponding to the second focus by using a second reverse mechanical index (MI) map that is obtained by reversing the second mechanical index (MI) map, so as to allow the mechanical index (MI) values, which are displayed on the second mechanical index (MI) map, to be a virtual second mechanical index (MI) value with respect to the depth values.

6. The method of claim 5, wherein the virtual first mechanical index (MI) value is decided based on a maximum mechanical index (MI) value of the first mechanical index (MI) map, and the virtual second mechanical index (MI) value is decided based on a maximum mechanical index (MI) value of the second mechanical index (MI) map.

7. The method of claim 6, further comprising:
   determining whether the virtual first mechanical index (MI) value and the virtual second mechanical index (MI) value are equal to each other; and
   if not equal, re-adjusting the adjusted gain value of the ultrasound echo signal corresponding to the first focus or the adjusted gain value of the ultrasound echo signal corresponding to the second focus, so as to allow the virtual first mechanical index (MI) value and the virtual second mechanical index (MI) value to be equal to each other.

8. The method of claim 5, wherein the method comprises:
   generating the ultrasound image of the target object by blending the ultrasound echo signal having the adjusted gain value corresponding to the first focus with the ultrasound echo signal having the adjusted gain value corresponding to the second focus; and
   displaying the ultrasound image.

9. The method of claim 5, further comprising adjusting a first ultrasound transmission voltage corresponding to the first focus or a second ultrasound transmission voltage corresponding to the second focus, so as to allow a first maximum mechanical index (MI) corresponding to the first focus and a second maximum mechanical index (MI) corresponding to the second focus to be equal to each other.

10. A non-transitory computer-readable recording medium having recorded thereon a program for executing the method of claim 1.

11. An ultrasound images correcting apparatus comprising:
a probe configured to output an ultrasound signal to a target object and receive an ultrasound echo signal corresponding to the ultrasound signal; and
a computer configured to:
obtain a mechanical index (MI) map indicating a correlation between depth values according to a travel direction of the ultrasound signal, and mechanical index (MI) values by the ultrasound signal, obtain a reverse mechanical index (MI) map by reversing the mechanical index (MI) map, and adjust a gain value of the ultrasound echo signal for each of the depth values by using the reverse mechanical index (MI) map.

12. The ultrasound images correcting apparatus of claim 11, wherein the computer is further configured to:
generate an ultrasound image of the target object based on the ultrasound echo signal having the adjusted gain value, and control a display to display the ultrasound image.

13. The ultrasound images correcting apparatus of claim 11, wherein the computer is further configured to:
obtain an acoustic pressure map indicating a correlation between depth values according to a travel direction of the ultrasound signal, and acoustic pressure values by the ultrasound signal, and adjust a gain value of an ultrasound echo signal corresponding to the ultrasound signal by using a reverse acoustic pressure map that is obtained by reversing the acoustic pressure map.

14. The ultrasound images correcting apparatus of claim 11, wherein the computer is further configured to:
obtain a thermal index (TI) map indicating a correlation between depth values according to a travel direction of the ultrasound signal, and thermal index (TI) values by the ultrasound signal, and adjust a gain value of an ultrasound echo signal corresponding to the ultrasound signal by using a reverse thermal index (TI) map that is obtained by reversing the thermal index (TI) map.

15. The ultrasound images correcting apparatus of claim 11, wherein the probe is further configured to:
output ultrasound signals having a first focus and a second focus; and
the computer is further configured to:
obtain a first mechanical index (MI) map and a second mechanical index (MI) map that correspond to the first focus and the second focus, respectively, adjust a gain value of an ultrasound echo signal corresponding to the first focus by using a first reverse mechanical index (MI) map that is obtained by reversing the first mechanical index (MI) map, so as to allow the mechanical index (MI) values, which are displayed on the first mechanical index (MI) map, to be a virtual first mechanical index (MI) value with respect to the depth values, and adjust a gain value of an ultrasound echo signal corresponding to the second focus by using a second reverse mechanical index (MI) map that is obtained by reversing the second mechanical index (MI) map, so as to allow the mechanical index (MI) values, which are displayed on the second mechanical index (MI) map, to be a virtual second mechanical index (MI) value with respect to the depth values.

16. The ultrasound images correcting apparatus of claim 15, wherein the virtual first mechanical index (MI) value is decided based on a maximum mechanical index (MI) value of the first mechanical index (MI) map, and the virtual second mechanical index (MI) value is decided based on a maximum mechanical index (MI) value of the second mechanical index (MI) map.

17. The ultrasound images correcting apparatus of claim 15, wherein the computer is further configured to:
determine whether the virtual first mechanical index (MI) value and the virtual second mechanical index (MI) value are equal to each other, and if not equal, re-adjust the adjusted gain value of the ultrasound echo signal corresponding to the first focus or the adjusted gain value of the ultrasound echo signal corresponding to the second focus, so as to allow the virtual first mechanical index (MI) value and the virtual second mechanical index (MI) value to be equal to each other.

18. The ultrasound images correcting apparatus of claim 15, wherein the computer is further configured to:
generate an ultrasound image of the target object by blending the ultrasound echo signal having the adjusted gain value corresponding to the first focus with the ultrasound echo signal having the adjusted gain value corresponding to the second focus, and control a display to display the ultrasound images.

19. The ultrasound images correcting apparatus of claim 15, wherein the computer is further configured to:
adjust a first ultrasound transmission voltage corresponding to the first focus or a second ultrasound transmission voltage corresponding to the second focus, so as to allow a first maximum mechanical index (MI) corresponding to the first focus and a second maximum mechanical index (MI) corresponding to the second focus to be equal to each other.

\* \* \* \* \*